United States Patent
Carson et al.

(10) Patent No.: US 6,953,479 B2
(45) Date of Patent: Oct. 11, 2005

(54) ORTHOPEDIC IMPLANT EXTENSION

(75) Inventors: Christopher Patrick Carson, Collierville, TN (US); Dwight T. Todd, Columbia, IN (US); Michael David Ries, Tiburon, CA (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 09/906,468

(22) Filed: Jul. 16, 2001

(65) Prior Publication Data

US 2003/0014120 A1 Jan. 16, 2003

(51) Int. Cl.[7] .................................................. A61F 2/38
(52) U.S. Cl. ............................... 623/20.15; 623/20.32; 623/20.35
(58) Field of Search .......................... 623/20.14, 20.15, 623/20.32, 20.34, 20.35, 20.36

(56) References Cited

U.S. PATENT DOCUMENTS

| 3,694,820 A | 10/1972 | Scales et al. |
| 3,803,641 A | 4/1974 | Golyakhovsky |
| 4,001,896 A | 1/1977 | Arkangel |
| 4,045,825 A | 9/1977 | Stroot |
| 4,106,130 A | 8/1978 | Scales |

(Continued)

FOREIGN PATENT DOCUMENTS

| DE | 163 476 | 6/1958 |
| DE | 29 27 880 | 2/1981 |
| DE | 43 20 086 A1 | 12/1994 |
| EP | 0 099 167 A1 | 1/1984 |
| EP | 0 177 755 A1 | 9/1985 |

(Continued)

OTHER PUBLICATIONS

Tornier Brochure entitled "Shoulder Prosthesis *Aequalis* . . . Adaptability", undated.
Tornier Brochure entitled "Prothese D'Epaule Aequalis Implant Humeral en Traumatologie", undated.
Tornier Brochure entitled "Introducing the Aequalis™ Shoulder Prosthesis . . . designed to reproduced your patient's individual anatomy", undated.

(Continued)

*Primary Examiner*—Ralph A. Lewis
(74) *Attorney, Agent, or Firm*—Kilpatrick Stockton LLP

(57) ABSTRACT

A stem extension for surgical implants such as tibial or femoral knee implants. The stem extension is interposed between the stem and its load bearing component (i.e., tibial tray or condylar component) and angularly orients the attached stem relative to the load bearing component to facilitate positioning of the stem in the bone canal and alignment of the load bearing component with the mechanical axis of the leg. The extension includes a female taper that engages the load bearing component. The extension also includes a male taper having a longitudinal axis oriented at an angle relative to the longitudinal axis of the female taper. Engagement of the male taper with the stem thereby orients the stem at an angle relative to the longitudinal axis of the load bearing component. Because the bone canal into which the stem is inserted is oftentimes angled relative to the mechanical axis of the leg, such orientation of the stem adjusts for the contour and/or angulation of the canal and facilitates positioning of the stem in the canal in a manner that promotes the desired alignment between the load bearing component and the mechanical axis of the leg, thereby allowing the implant to more closely replicate the geometry of the knee and leg. In addition to being oriented angularly, the female and male taper of the extension may also be offset parallel to facilitate insertion of the stem into canals that are not only angled relative to, but also offset from, the mechanical axis of the leg.

25 Claims, 5 Drawing Sheets

U.S. PATENT DOCUMENTS

| | | | |
|---|---|---|---|
| 4,135,517 | A | 1/1979 | Reale |
| 4,179,758 | A | 12/1979 | Gristina |
| 4,224,695 | A | 9/1980 | Grundei et al. |
| 4,268,920 | A * | 5/1981 | Engelbrecht et al. |
| 4,538,305 | A | 9/1985 | Engelbrecht et al. |
| 4,676,797 | A | 6/1987 | Anapliotis et al. |
| 4,676,798 | A | 6/1987 | Noiles |
| 4,714,476 | A | 12/1987 | Ranawat et al. |
| 4,731,086 | A | 3/1988 | Whiteside et al. |
| 4,790,854 | A | 12/1988 | Harder et al. |
| 4,822,365 | A | 4/1989 | Walker et al. |
| 4,822,366 | A | 4/1989 | Bolesky |
| 4,834,081 | A | 5/1989 | Van Zile |
| 4,865,605 | A | 9/1989 | Dines et al. |
| 4,883,488 | A | 11/1989 | Bloebaum et al. |
| 4,919,670 | A | 4/1990 | Dale et al. |
| 4,936,853 | A | 6/1990 | Fabian et al. |
| 4,944,764 | A | 7/1990 | Stossel |
| 4,950,297 | A | 8/1990 | Elloy et al. |
| 4,950,298 | A | 8/1990 | Gustilo et al. |
| 4,959,071 | A | 9/1990 | Brown et al. |
| 4,963,155 | A | 10/1990 | Lazzeri et al. |
| 4,985,037 | A | 1/1991 | Petersen |
| 5,002,578 | A | 3/1991 | Luman |
| 5,071,438 | A | 12/1991 | Jones et al. |
| 5,100,407 | A | 3/1992 | Conrad et al. |
| 5,123,928 | A | 6/1992 | Moser |
| 5,133,760 | A | 7/1992 | Petersen et al. |
| 5,133,763 | A | 7/1992 | Mullers |
| 5,135,529 | A | 8/1992 | Paxson et al. |
| 5,139,521 | A | 8/1992 | Schelhas |
| 5,152,796 | A | 10/1992 | Slamin |
| 5,194,066 | A | 3/1993 | Van Zile |
| 5,207,711 | A | 5/1993 | Caspari et al. |
| 5,226,915 | A | 7/1993 | Bertin |
| 5,271,737 | A | 12/1993 | Baldwin et al. |
| 5,290,313 | A | 3/1994 | Heldreth |
| 5,314,479 | A | 5/1994 | Rockwood, Jr. et al. |
| 5,330,534 | A | 7/1994 | Herrington et al. |
| 5,358,526 | A | 10/1994 | Tornier |
| 5,387,240 | A | 2/1995 | Pottenger et al. |
| 5,462,563 | A | 10/1995 | Shearer et al. |
| 5,489,309 | A | 2/1996 | Lackey et al. |
| 5,507,814 | A | 4/1996 | Gilbert et al. |
| 5,507,817 | A | 4/1996 | Craig et al. |
| 5,545,228 | A | 8/1996 | Kambin |
| 5,549,682 | A | 8/1996 | Roy |
| 5,549,703 | A | 8/1996 | Daigle et al. |
| 5,556,433 | A | 9/1996 | Gabriel et al. |
| 5,569,263 | A | 10/1996 | Hein |
| 5,580,352 | A | 12/1996 | Sekel |
| 5,593,449 | A * | 1/1997 | Roberson, Jr. |
| 5,613,970 | A | 3/1997 | Houston et al. |
| 5,702,457 | A | 12/1997 | Walch et al. |
| 5,743,918 | A | 4/1998 | Calandruccio et al. |
| 5,766,261 | A | 6/1998 | Neal et al. |
| 5,782,920 | A | 7/1998 | Colleran |
| 5,885,299 | A | 3/1999 | Winslow et al. |
| 5,902,340 | A | 5/1999 | White et al. |
| 5,906,644 | A | 5/1999 | Powell |
| 6,063,091 | A * | 5/2000 | Lombardo et al. ............ 606/88 |
| 6,068,122 | A * | 5/2000 | Burns et al. |
| 6,129,764 | A | 10/2000 | Servidio |
| 6,146,424 | A * | 11/2000 | Gray, Jr. et al. ......... 623/20.34 |
| 6,149,687 | A * | 11/2000 | Gray, Jr. et al. ......... 623/20.34 |
| 6,162,255 | A * | 12/2000 | Oyola ..................... 623/20.34 |
| 6,171,342 | B1 * | 1/2001 | O'Neil et al. ............ 623/20.15 |
| 6,197,063 | B1 | 3/2001 | Dews |
| 6,214,052 | B1 | 4/2001 | Burkinshaw |
| 6,228,120 | B1 | 5/2001 | Leonard et al. |
| 6,423,096 | B1 * | 7/2002 | Musset et al. ........... 623/20.15 |

FOREIGN PATENT DOCUMENTS

| | | |
|---|---|---|
| EP | 0 363 019 A2 | 4/1990 |
| EP | 0 457 222 A1 | 5/1991 |
| EP | 0 679 375 A1 | 11/1995 |
| EP | 0 853 930 A2 | 7/1998 |
| EP | 0 679 375 | 9/1998 |
| EP | 0 931 522 A1 | 7/1999 |
| EP | 0 712 617 | 9/1999 |
| EP | 0 940 126 A1 | 9/1999 |
| EP | 0 993 813 A2 | 4/2000 |
| EP | 1 048 274 A2 | 11/2000 |
| EP | 1 082 943 A2 | 3/2001 |
| FR | 2 288 509 | 5/1976 |
| FR | A 2 664 809 | 1/1992 |
| FR | 2 669 214 | 5/1992 |
| FR | 2 685 633 | 7/1993 |
| FR | 2 697 996 | 5/1994 |
| FR | 2 763 501 | 11/1998 |
| FR | 2 773 469 | 7/1999 |
| GB | 1 575 278 | 9/1980 |
| GB | 2 253 147 A | 9/1992 |
| GB | 2 334 890 A | 3/1999 |
| WO | 2 721 200 | 12/1995 |
| WO | WO 96/17553 | 6/1996 |
| WO | WO 98/46172 | 10/1998 |
| WO | WO 00/06056 | 2/2000 |

OTHER PUBLICATIONS

Smith & Nephew Orthopaedics—Performance. Innovation. Trust. Brochure entitled "Neer II™ total shoulder system" (2000).

Smith & Nephew Orthopaedcs—Performance. Innovation. Trust. Brochure entitled "ideas in motion Modular Shoulder System" (2000).

Smith & Nephew Brochure entitled "Cofield[2] Total Shoulder System—Surgical Technique" pp. 1–32 (May 1997).

Smith & Nephew Brochure entitled "Cofield[2] Total Shoulder System Making a Positive Impact on Shoulder Replacement" (Nov. 1996).

Smith & Nephew Brochure entitled "An Accurate, Reproducible, and Simple Solution to Complex Surgery Cofield[2] Total Shoulder System" pp. 1–22 (Dec. 1998).

Bechtold,, Joan, "Cross–Sectional Geometry of Tibiae," (1989).

McCormack, Damian, "Mechanical Axis Deviation: Definitions, Measurements and Consequences," http://www.iol.ie/~rcsiorth/journal/volume2/issue5/mech.htm (Aug. 30, 2000).

Hicks, *CORR*, vol. 321:111–116 (1995).

Ries, *J. Arthr.*, 13(1) (1998).

Stryker Howmedica Osteonics Total Knee Arthroplasty Total Stabilizer, http://www.osteonics.com/osteonics/knees/tsknee/tib.html (Feb. 17, 2000), p. 1.

Stryker Howmedica Osteonics Total Knee Arthroplasty Total Stabilizer, http://www.osteonics.com/osteonics/knees/tsknee/fem.html (Feb. 17, 2000), p. 1.

International Serach Report in related PCT/US01/22724.

* cited by examiner

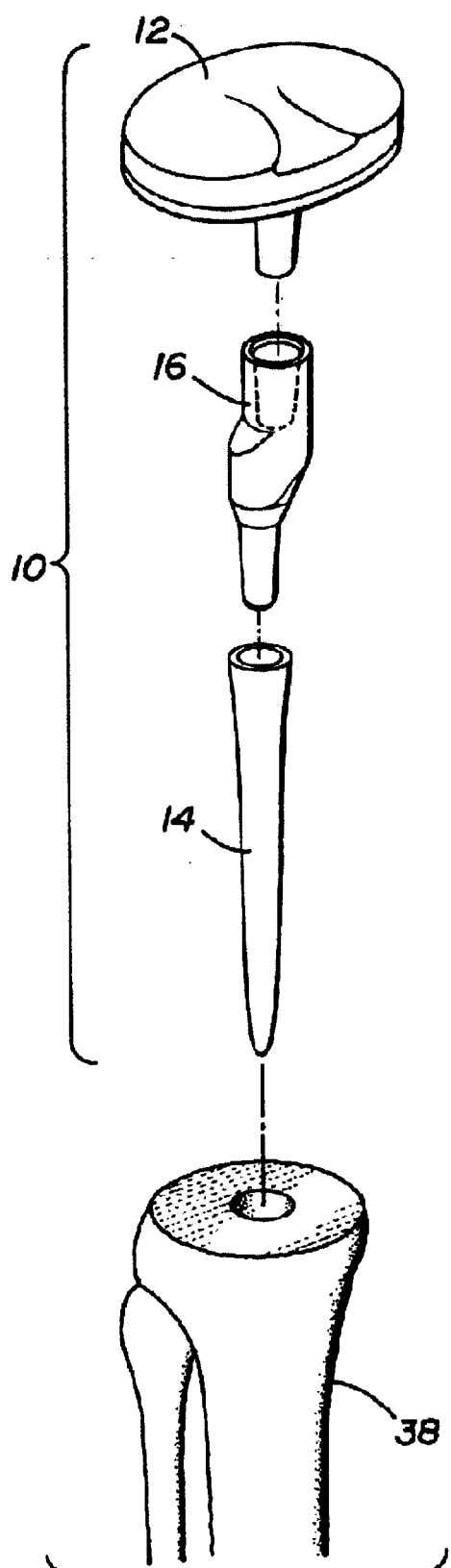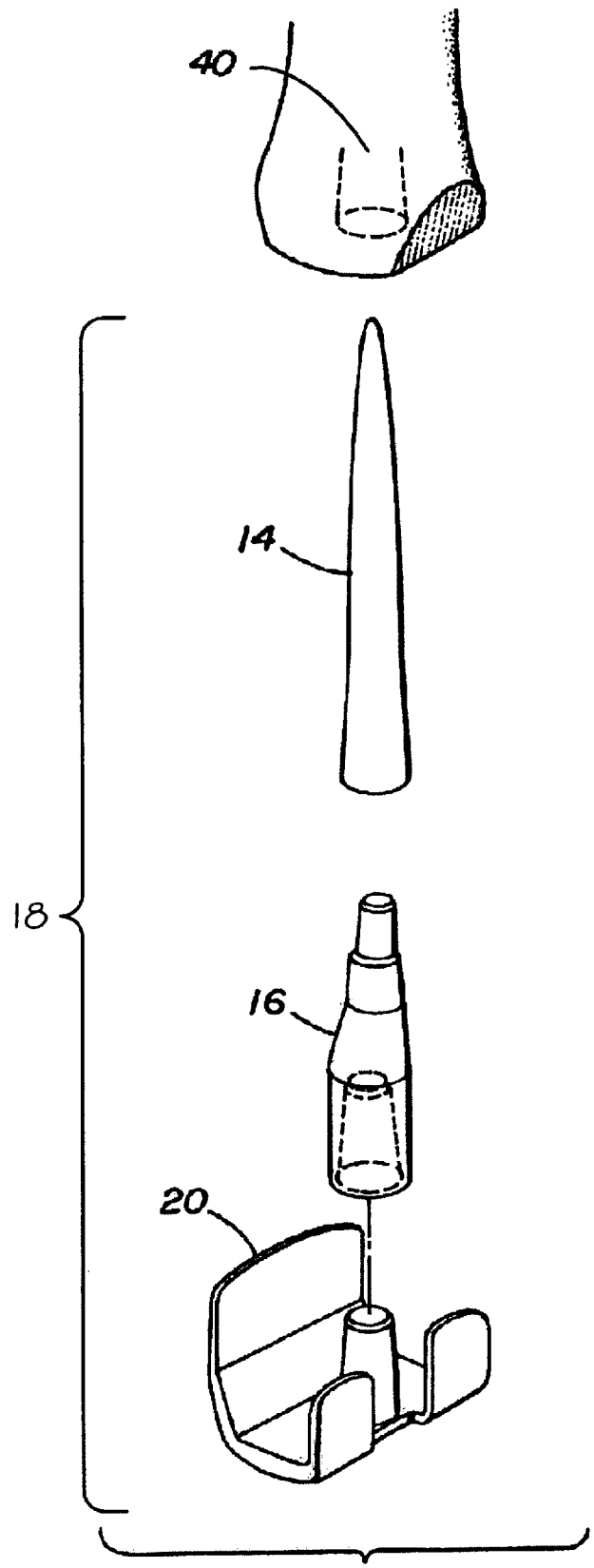

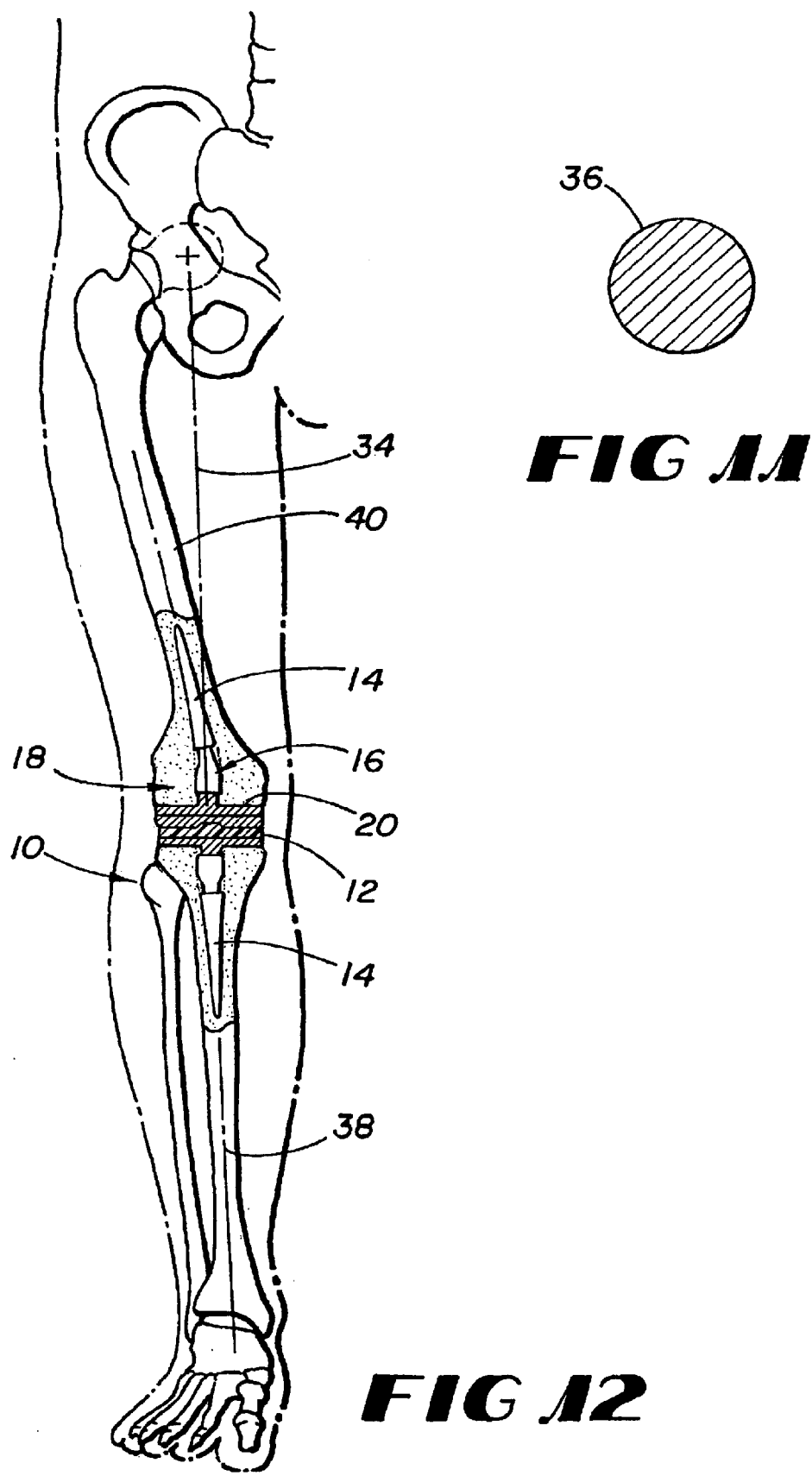

ORTHOPEDIC IMPLANT EXTENSION

FIELD OF THE INVENTION

This invention relates generally to an intermediate stem extension that connects a stem to a tibial and/or femoral load bearing component of a tibial/femoral orthopedic implant. The stem extension has a female taper which engages the tibial and/or femoral load bearing component and a male taper which engages the stem and which is offset from and angled relative to the female taper to orient the stem and thus facilitate reception of the stem in a bowed or angled tibial or femoral canal.

BACKGROUND OF THE INVENTION

Orthopedic implants, such as knee implants, typically include a tibial implant and a femoral implant. The tibial implant generally includes a load bearing component (such as a tibial plate) which may be connected to a stem to be received in the tibial canal to stabilize the load bearing component. The femoral implant includes a load bearing component (such as a condylar component) which is connected to the distal end of the femur. The femoral load bearing component is sometimes connected to a stem which is received in the femoral canal to stabilize the load bearing component.

The tibial plateau and the condyles of the femur bearing on the tibial plateau act similar to a hinge within the knee to allow bending and other movement of the knee. Optimal movement and operation of the knee is achieved when both the tibial plateau and the condyles are aligned with the mechanical axis of the leg (defined as the line from the center of the femoral head to the center of the ankle). The tibial load bearing component and the femoral load bearing component ultimately cooperate with each other to replicate as closely as possible the action and relationship of the tibial plateau and the condyles of the femur bearing on it. Just as with an actual knee, the success of such implants depends at least partially on their positioning within the knee so that the longitudinal axes of the tibial load bearing component and the femoral load bearing component are aligned with the mechanical axis of the leg.

Very briefly, to implant the tibial and femoral implants into the knee, the surgeon first reams the intramedullary canals of the femur and tibia. Then, the proximal surfaces of the tibia and the distal surfaces of the femur are prepared for receiving the implants. Trial reduction usually follows to assess bone preparation and to select properly sized and configured tibial and femoral implants. The actual tibial and femoral implants are then assembled and implanted into the knee.

The tibial and femoral canals are not always aligned with, but rather are generally offset parallel a distance from, the mechanical axis of the leg. Because of such parallel offset, when a stem is inserted into an offset canal, the attached load bearing component is not aligned with, but rather is offset from, the mechanical axis of the leg. To accommodate for such offset canals, some stems, such as those disclosed in U.S. Pat. No. 5,290,313 to Heldreth and PCT Application No. WO 00/06056, are formed with two longitudinal axes offset from each other so that one axis runs through the center of the tibial or femoral load bearing component and the other axis is aligned with the offset tibial or femoral canal. In this way, when a stem is inserted into a canal offset from the mechanical axis of the leg, the longitudinal axis of the load bearing component may still be aligned with the mechanical axis of the leg. Although offset, the axes of such stems, however, are still parallel to each other.

While the stem may connect directly to the tibial or femoral load bearing component, intermediate stem extensions, such as those disclosed in U.S. Pat. No. 5,782,920 to Colleran, have been used to connect the stems and components. Colleran discloses a tibial prosthesis that includes a tibial tray, a stem, and a stem extension that connects the stem to the tibial tray. In contrast to the Heldreth-type stems with offset longitudinal axes, the stem in Colleran has, like most stems, a single longitudinal axis. The Colleran stem extension, rather than the actual stem, is the component which features offset longitudinal axes. When the system is assembled, the desired parallel offset between the stem and the tibial tray is obtained by virtue of the stem extension. Again, however, the axis of the stem is parallel to the axis of the tibial tray and to the mechanical axis of the leg.

Studies have shown, however, that in addition to being offset from the mechanical axis, the tibial and femoral canals are not always disposed parallel to the mechanical axis of the leg. Rather, across a population of humans, a valgus bowing of the tibia exists from about $1.63°+/-1.57°$ relative to the mechanical axis. Consequently, if a stem oriented parallel to the mechanical axis is inserted into the bowed tibial canal, the stem can impinge on the lateral cortex of the tibial canal proximal to the knee and the medial cortex distal to the knee. Similarly, the femoral canal can bow posteriorly relative to the mechanical axis, which results in impingement by the stem of the anterior cortex of the femoral canal in the diaphysis of the femur and the posterior cortex slightly superior to the knee. Such impingement can prevent adequate penetration of the canal by the stem and result in improper positioning of the tibial and femoral components in the knee.

Improper positioning of the component with respect to the bone can have grave effects, including stress shielding and bone loss due to nonuniform transfer of load from the bone to the stem, and can also limit range of motion. Insertion of a stem into an angled tibial canal may result in the misalignment of the tibial component with the tibial plateau so that a part of the tibial component hangs over the tibial plateau. Such overhang can lead to the tibial component rubbing the soft tissue surrounding the knee, causing irritation and pain. Moreover, a consequence of overhang by one side of the tibial component is underhang by the other side of the tibial component, so that the underhang portion of the component is resting on the softer cancellous bone instead of the harder cortical bone along the peripheral rim of the tibial plateau. The component consequently may sink into the softer bone, causing the entire component to tilt toward the side of underhang. This can jeopardize the stability of the implant.

Furthermore, the orientation of the femoral canal is such that when the stem and connected femoral cutting block is inserted, the femoral resection may notch the anterior cortex, predisposing the femur to fracture. More often, however, the orientation of the canal forces the femoral component's anterior flange to sit proud on the anterior cortex, thereby creating a gap between the anterior flange of the component and the anterior cortex of the femur. Traditionally the gap has been filled with bone cement, bone graft, or a metal shim or augment. This step of filling the gap adds time to the procedure.

To prevent such adverse effects by better positioning the stem into the bowed canal, surgeons often will select a smaller diameter stem that can be inserted the requisite distance into the canal without impinging the bone unduly or in undesired places. However, use of a smaller diameter stem compromises the fit between the stem and the canal, which can lead to movement of the stem within the canal. Such movement can result in undesired shifting of the attached load bearing component relative to the bone so that the component is located in an undesirable position within the knee. It can also result in instability of the prosthesis in general, excess wear, and other adverse effects.

Surgeons who choose not to downsize the diameter of the stem sometimes, perhaps unknowingly, rotate the femoral or tibial load bearing component and the attached stem to orient the stem relative to the canal to permit deeper penetration of the canal by the stem. This can also result in undesirable positioning of the load bearing component and consequent effects such as those disclosed above.

SUMMARY OF THE INVENTION

The present invention addresses the issues discussed above by providing an intermediate stem extension that angularly orients an attached tibial or femoral implant stem relative to its corresponding load bearing component (e.g., tibial tray, condylar component) to facilitate positioning of the stem in a bowed or angled tibial or femoral canal in a manner that allows closer correspondence between the geometry of the implant components and the geometry of the tibia, femur, and knee, and better alignment of the load bearing components with the mechanical axis of the leg.

The extension includes a female taper that engages the tibial and/or femoral load bearing component so that the longitudinal axis of the female taper is aligned with the longitudinal axis of the load bearing component (which, when implanted into the knee, should also be aligned with the mechanical axes of the leg). The extension also includes a male taper having a longitudinal axis oriented at an angle relative to the female taper's longitudinal axis. Engagement of the male taper with the stem thereby orients the stem at an angle relative to the female taper's and the load bearing component's aligned longitudinal axes. This angulation of the stem facilitates insertion of the stem into a tibial or femoral canal that is angled relative to the mechanical axis of the leg, while still promoting the desired alignment of the longitudinal axis of the load bearing component with the mechanical axis of the leg. Such angled orientation of the stem compensates for the contour and/or angulation of the canal and facilitates positioning of the stem into the canal in a manner that allows closer correspondence between the geometry of the implant components and the geometry of the tibia, femur, and knee. In addition to having an angled orientation, the male taper may also be offset parallel from the female taper to facilitate positioning of the stem in canals that are not only angled relative to, but also offset parallel from, the mechanical axis of the leg.

According to the present invention, there is provided a tibial implant comprising:

a. a stem adapted to be fitted into a tibial canal;
 b. a load bearing component having a longitudinal axis and adapted to approximate the size and shape of a tibial plateau; and
 c. an intermediate stem extension for operatively connecting the stem to the load bearing component, wherein the extension is adapted to apply angular orientation in a manner that causes the load bearing component to be positioned within a leg in a manner wherein the longitudinal axis of the load bearing component is substantially aligned with the mechanical axis of the leg.

According to the present invention, there is provided a femoral implant comprising:

a. a stem adapted to be fitted into a femoral canal;
 b. a load bearing component having a longitudinal axis and adapted to approximate the size and shape of condyles of a femur; and
 c. an intermediate stem extension for operatively connecting the stem to the load bearing component, wherein the extension is adapted to apply an angular orientation in a manner that causes the load bearing component to be positioned within a leg in a manner wherein the longitudinal axis of the load bearing component is substantially aligned with the mechanical axis of the leg.

According to the present invention, there is provided a knee implant system comprising:

a. a tibial stem adapted to be fitted into a tibial canal;
 b. a tibial load bearing component adapted to approximate the size and shape of a tibial plateau;
 c. an tibial intermediate stem extension for operatively connecting the tibial stem to the tibial load bearing component, the extension comprising a central body having a female taper and a male taper, wherein the female taper has a longitudinal axis and the male taper has a longitudinal axis disposed at an angle relative to the longitudinal axis of the female taper;
 d. a femoral stem adapted to be fitted into a femoral canal; and
 e. a femoral load bearing component adapted to approximate the size and shape of condyles of a femur.

According to the present invention, there is provided a method of installing a knee implant comprising:

a. preparing a proximal portion of the tibia and tibial canal of a patient;
 b. preparing a distal portion of the femur and femoral canal of the patient;
 c. performing trial reduction in order to select a tibial implant and a femoral implant for the tibia and femur, respectively;
 d. introducing the tibial implant into the tibial canal, the tibial implant comprising:
   a tibial stem adapted to be fitted into a tibial canal;
   a tibial load bearing component adapted to approximate the size and shape of a tibial plateau; and
   an tibial intermediate stem extension for operatively connecting the tibial stem to the tibial load bearing component, the extension comprising a central body having a female taper and a male taper, wherein the female taper has a longitudinal axis and the male taper has a longitudinal axis disposed at an angle relative to the longitudinal axis of the female taper; and
 e. introducing the femoral implant into the femoral canal, the femoral implant comprising:
   a femoral stem adapted to be fitted into a femoral canal; and
   a femoral load bearing component adapted to approximate the size and shape of condyles of a femur and operatively connect with the femoral stem.

According to the present invention, there is provided a prosthesis kit for replacement of a knee, comprising:

a. a stem adapted to be fitted into a tibial canal;
 b. a load bearing component adapted to approximate the size and shape of a tibial plateau; and
 c. a plurality of intermediate stem extensions of which one may be selected to connect the stem to the load bearing component, each intermediate stem extension comprising a central body comprising:

a female taper having a longitudinal axis;

a male taper having a longitudinal axis, wherein the longitudinal axis of the male taper is disposed at an angle relative to the longitudinal axis of the female taper and offset parallel a first distance from the longitudinal axis of the female taper at a second distance from a bottom of the female taper.

According to the present invention, there is provided a prosthesis kit for replacement of a knee, comprising:

a. a stem adapted to be fitted into a femoral canal;

b. a load bearing component adapted to approximate the size and shape of condyles of a femur; and c. a plurality of intermediate stem extensions of which one may be selected to connect the stem to the load bearing component, each intermediate stem extension comprising a central body comprising:

a female taper having a longitudinal axis;

a male taper having a longitudinal axis, wherein the longitudinal axis of the male taper is disposed at an angle relative to the longitudinal axis of the female taper and offset parallel a first distance from the longitudinal axis of the female taper at a second distance from a bottom of the female taper.

It is an object of the present invention to provide an implant stem extension which facilitates positioning of an implant stem in a tibial and/or femoral canal in a manner that allows closer correspondence between the geometry of the implant components and the geometry of the tibia, femur, and knee.

It is another object of the present invention to provide an implant stem extension which facilitates positioning of an implant stem in a tibial and/or femoral canal in a manner that promotes alignment of the longitudinal axis of a load bearing component with the mechanical axis of the leg.

It is yet another object of the present invention to provide an implant stem extension which improves the fit between a tibial or femoral stem and a tibial and/or femoral canal, respectively, and thereby stabilizes the implant in the knee.

It is still another object of the present invention to provide a stem extension that minimizes undue impingement by the stem within the intramedullary cortex of the tibia and/or femur and consequent effects.

Other objects, features, and advantages of the present invention will be apparent with respect to the remainder of this document.

BRIEF DESCRIPTION OF THE DRAWINGS

FIG. 1 is a perspective view of one embodiment of the tibial implant of the present invention.

FIG. 2 is a perspective view of one embodiment of the femoral implant of the present invention.

FIG. 11 is a cross-section taken along line 11—11 in FIG. 9.

FIG. 12 is a front cross-sectional view of a knee illustrating an implanted tibial and femoral implant, both having the stem extension according to the present invention.

DETAILED DESCRIPTION OF THE DRAWINGS

Figure 3:
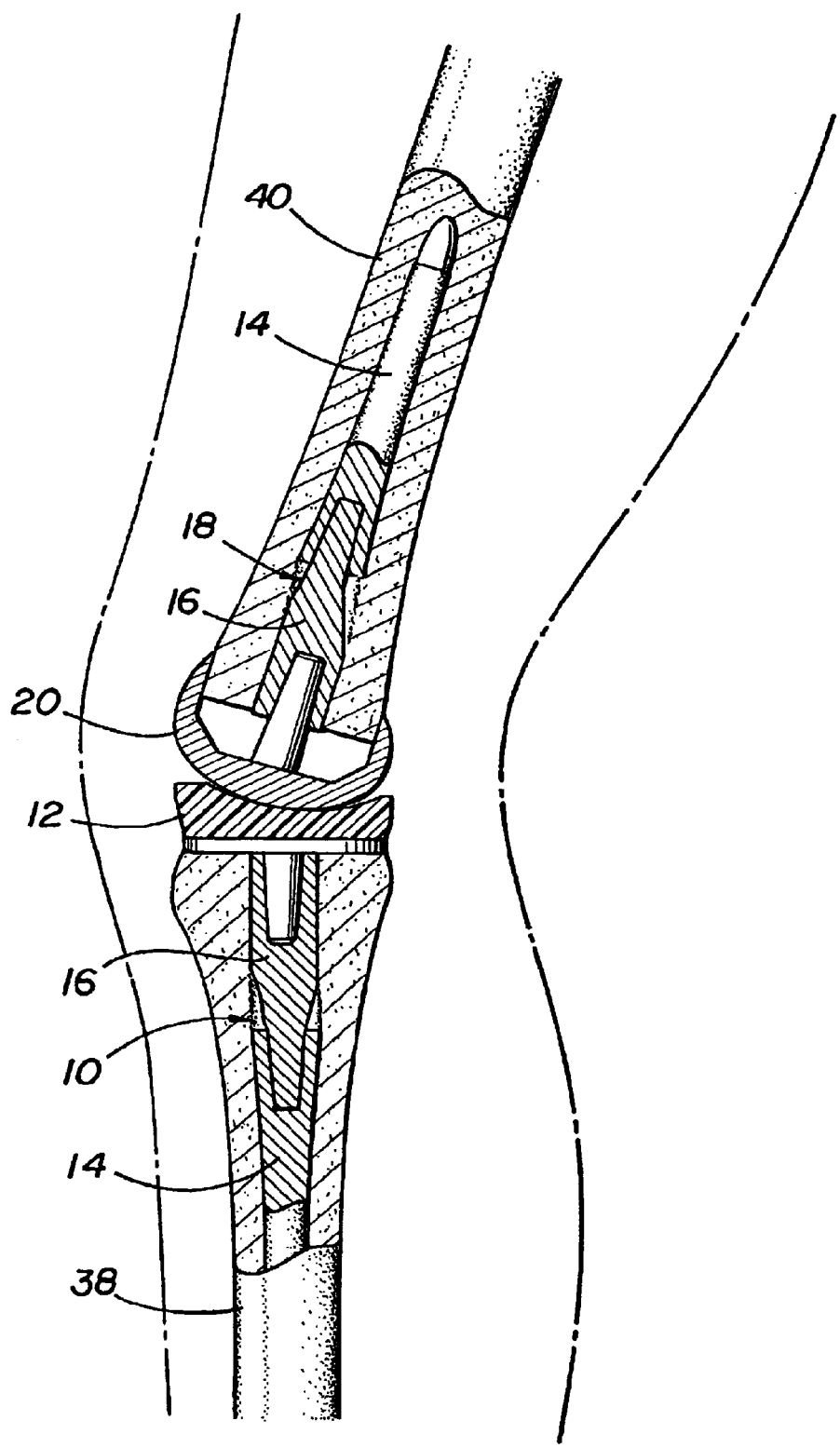
FIG. 3 is a side cross-sectional view of a knee illustrating an implanted tibial and femoral implant, both having the stem extension according to the present invention.
Figure 4:
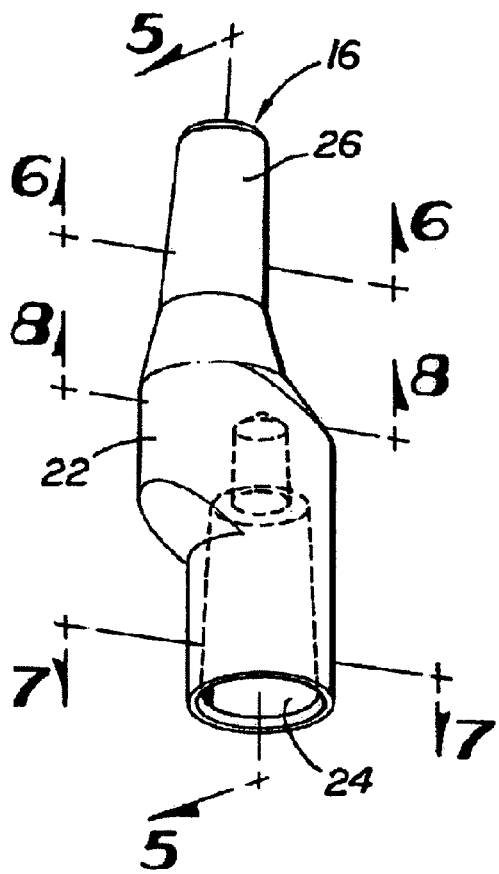
FIG. 4 is a perspective view of one embodiment of the stem extension of the present invention.
Figure 5:
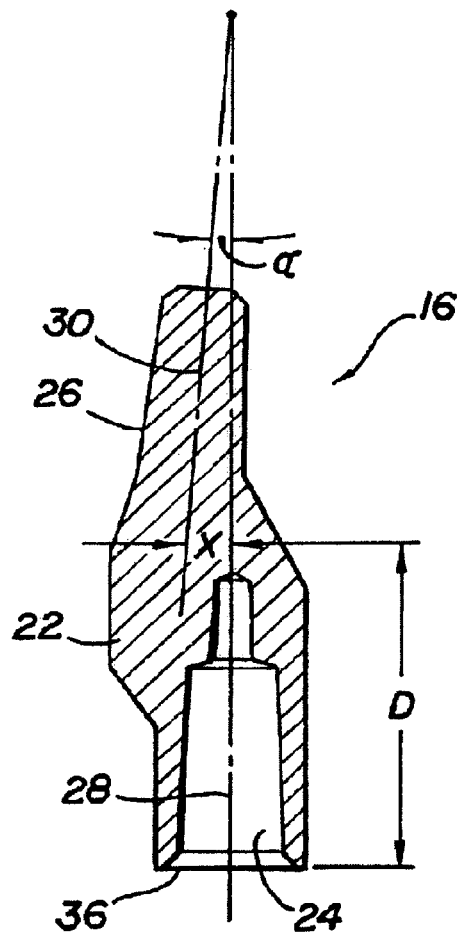
FIG. 5 is a cross-section taken along line 5—5 in FIG. 4.

FIG. 1 illustrates an embodiment of a tibial implant 10 according to the present invention. Tibial implant 10 comprises a tibial load bearing component 12 (ex. tibial tray or platform), a stem 14, and a stem extension 16. The extension 16 connects the tibial load bearing component 12 and the stem 14. Similarly, FIG. 2 illustrates an embodiment of a femoral implant 18 according to the present invention, comprising a femoral load bearing component 20 (ex. condylar component) and a stem 14. The femoral implant 18 may also include a stem extension 16 connecting the femoral load bearing component 20 and the stem 14 (as shown in FIG. 2). FIG. 3 shows a tibia 38 and femur 40 into which a tibial implant 10 and femoral implant 18 have been implanted. While not necessary, a stem extension 16 has been used in both the tibial implant 10 and the femoral implant 18 to connect the stems 14 to their respective tibial and femoral load bearing components 12, 20.

FIGS. 4–8 illustrate one embodiment of the stem extension 16. The extension 16 may be made from a variety of materials possessing suitable physical properties including structural integrity and adequate strength, but is preferably made from an alloy, such as titanium (Ti-6Al-4V) or cobalt chromium (CoCr).

The extension 16 has a central body 22 with a female taper 24 and a male taper 26. The male taper 26 may be, but does not have to be, integrally-formed with the central body 22. The female taper 24 couples with the load bearing component 12, 20 and the male taper 26 couples with the stem 14 (see FIGS. 1–3). Note, however, that in an alternative embodiment, this configuration could be reversed, i.e. the male taper 26 could couple with the load bearing component 12, 20 and the female taper 24 could couple with the stem 14.

Figure 6:
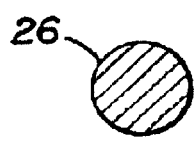
FIG. 6 is a cross-section taken along line 6—6 in FIG. 4.
Figure 7:
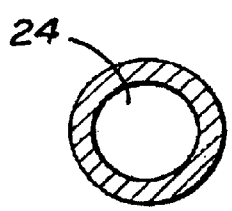
FIG. 7 is a cross-section taken along line 7—7 in FIG. 4.
Figure 8:
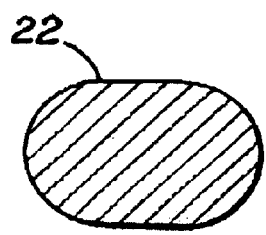
FIG. 8 is a cross-section taken along line 8—8 in FIG. 4.

The exterior of the male taper 26 and the interior of the female taper 24 are preferably Morse tapers, having generally circular cross sections (see FIGS. 6 and 7). The circular cross-section of the tapers 24, 26 facilitates rotation and other adjustment of the stem extension 16 relative to the load bearing component 12, 20 and/or the stem 14 to better position the stem 14 within the canal. The walls of the tapers 24, 26 stabilize the stem extension 16 relative to the load bearing component 12, 20 and/or the stem 14 when the desired position is attained. Note, however, that the female and male taper 24, 26 may be any shape or combination of shapes appropriate to couple with the stem 14 and the load bearing component 12, 20. Moreover, the cross-sections of the female and male taper 24, 26 in a single extension 16 may be of different shapes. Additionally, the area of the cross-sections of the tapers 24, 26 may remain constant or vary along the length of the extension 16, depending on the shape of the parts to which they will mate on the load bearing component 12, 20 and the stem 14.

Figure 9:
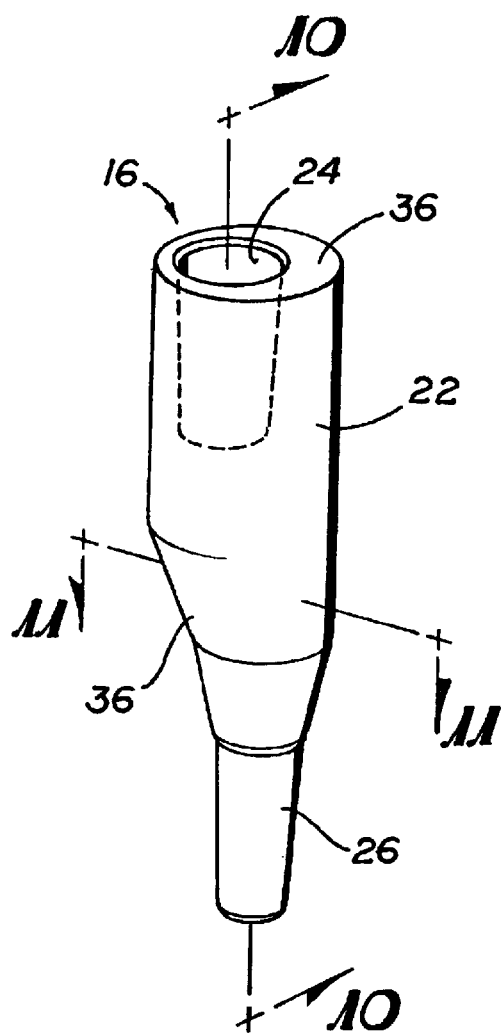
FIG. 9 is a perspective view of another embodiment of the stem extension of the present invention.
Figure 10:
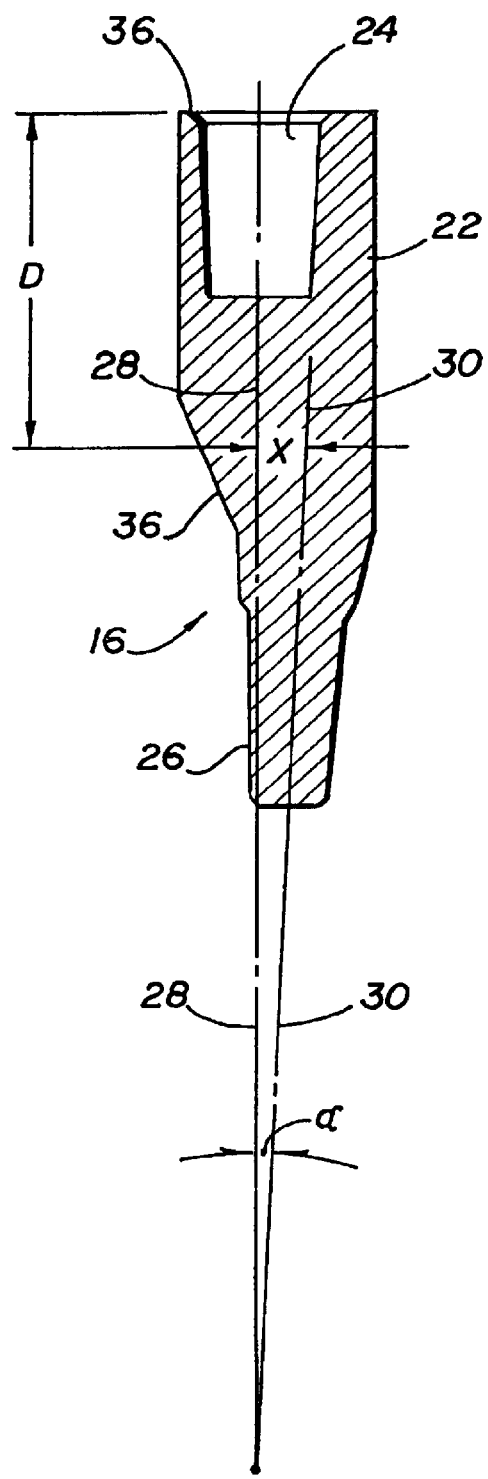
FIG. 10 is a cross-section taken along line 10—10 in FIG. 9.

The central body 22 may assume a variety of shapes as well. In the embodiment shown in FIGS. 4–8, the central body 22 is oval-shaped (see FIG. 8). In an alternative embodiment shown in FIGS. 9–11, the central body is circular-shaped (see FIG. 11).

The female and male tapers 24, 26 are oriented angularly relative to each other. Longitudinal axes 28, 30 run through the center of the female taper 24 and the male taper 26, respectively, in a manner to form the center of rotation of each of the tapers. The longitudinal axes 28, 30 are not parallel. The angular orientation, expressed in degrees, represents the angle (α) between the longitudinal axes 28, 30 of the female and male tapers 24, 26.

Moreover, the female and male tapers 24, 26 are preferably, but do not have to be, offset from each other. The parallel offset (x), expressed in millimeters, represents the distance between the longitudinal axis 28 of the female taper 24 and the longitudinal axis 30 of the male taper 26 at a certain distance (D) from the bottom 36 of the female taper 24.

Because the desired parallel offset and angular orientation will vary depending on the patient, preferred values for x and α could vary. However, studies and experimentation have revealed that the parallel offset (x) is preferably between 1 and 15 millimeters at a distance (D) between 1 and 100 mm, but preferably at a distance (D) between 10 and 50 mm. Moreover, the angular orientation (α) is preferably between 1° and 10°. Stem extensions 16 may be offered with different permutations of parallel offsets and angles.

When the female taper 24 engages the load bearing component 12, 20, the longitudinal axis 28 of the female taper 24 is aligned with both the longitudinal axis of the load bearing component 12, 20 and with the mechanical axis of the leg 34 (see FIG. 12). The longitudinal axis 30 of the male taper 26, and consequently the longitudinal axis of the stem 14 mounted onto the male taper 26, is angled relative to the mechanical axis of the leg. When the stem 14 is inserted into a canal, its angled orientation allows it to better follow and fit within the angled or bowed contour of the canal, thereby significantly reducing or eliminating undue impingement by the stem 14 on the canal without compromising (and even facilitating) the fit between the stem 14 and the canal and the overall stability of the implant. The angled stem also facilitates the desired alignment between the load bearing component 12, 20 and the mechanical axis of the leg.

In addition to being angled relative to the mechanical axis of the leg, the longitudinal axis 30 of the male taper 26, and consequently the longitudinal axis of the stem 14 mounted onto the male taper 26, may also be offset from the mechanical axis of the leg. The stem 14 can therefore be positioned in the canal in a manner that allows closer correspondence between the geometry of the implant components and that facilitates the desired alignment between the load bearing component 12, 20 and the mechanical axis of the leg.

The foregoing is provided for the purpose of illustrating, explaining and describing embodiments of the present invention. Further modifications and adaptations to these embodiments will be apparent to those skilled in the art and may be made without departing from the spirit of the invention or the scope of the following claims.

What is claimed is:

1. A tibial implant comprising:
   a. a stem adapted to be fitted into a tibial canal;
   b. a load bearing component having a longitudinal axis and adapted to approximate the size and shape of a tibial plateau; and
   c. an intermediate stem extension for operatively connecting the stem to the load bearing component, wherein the extension has a first taper with a first longitudinal axis and a second taper with a second longitudinal axis, wherein the first axis and the second axis are non-parallel to one another such that the intermediate stem extension is adapted to apply angular orientation in a manner that causes the load bearing component to be positioned within a leg in a manner wherein the longitudinal axis of the load bearing component is substantially aligned with the mechanical axis of the leg.

2. The tibial implant of claim 1, wherein the first taper comprises a male taper for engaging the stem and the second taper comprises a female taper for engaging the load bearing component, wherein, when the implant is so assembled and implanted into the leg, the stem is oriented at an angle to the mechanical axis of the leg.

3. The tibial implant of claim 1, wherein the stem extension is adapted to apply parallel offset in a manner that causes the load bearing component to be positioned within the leg in a manner wherein the longitudinal axis of the load bearing component is substantially aligned with the mechanical axis of the leg.

4. The tibial implant of claim 3, wherein the first taper comprises a male taper for engaging the stem and the second taper comprises a female taper for engaging the load bearing component, wherein, when the implant is so assembled and implanted into the leg, the stem is oriented at an angle to and offset parallel from the mechanical axis of the leg.

5. The tibial implant of claim 1, wherein the extension comprises a central body and wherein the first and second tapers comprise a female taper and a male taper, wherein the female taper has a longitudinal axis and the male taper has a longitudinal axis disposed at an angle relative to the longitudinal axis of the female taper.

6. The tibial implant of claim 5, wherein the angle is at least about 1°.

7. The tibial implant of claim 6, wherein the angle is no more than about 10°.

8. The tibial implant of claim 5, wherein a cross-section of the female taper and a cross-section of the male taper are substantially different shapes.

9. The tibial implant of claim 5, wherein a cross-section of the female taper and a cross-section of the male taper are the substantially identical shape.

10. The tibial implant of claim 9, wherein the shape is substantially circular.

11. The tibial implant of claim 5, wherein the cross-sectional area of the female taper and the cross-sectional area of the male taper vary along the length of the extension.

12. The tibial implant of claim 5, wherein the cross-sectional area of the female taper and the cross-sectional area of the male taper have a substantially constant slope along the length of the extension, such that the female taper and the male taper are slight tapers.

13. The tibial implant of claim 5, wherein the female taper operatively engages the load bearing component and the male taper operatively engages the stem.

14. The tibial implant of claim 5, wherein the extension comprises an alloy.

15. The tibial implant of claim 14, wherein the alloy is titanium.

16. The tibial implant of claim 5, wherein the male taper is integrally-formed with the central body.

17. The tibial implant of claim 5, wherein the longitudinal axis of the male taper is offset parallel a first distance from the longitudinal axis of the female taper at a second distance from a bottom of the female taper.

18. The tibial implant of claim 17, wherein the first distance is between 1 millimeter and 15 millimeters when the second distance is between 1 and 100 millimeters.

19. The tibial implant of claim 18, wherein the first distance is between 1 millimeter and 10 millimeters when the second distance is between 10 and 50 millimeters.

20. The tibial implant of claim 17, wherein the first distance is approximately zero when the second distance is between 1 and 100 millimeters.

21. A knee implant system comprising:
   a. a tibial stem adapted to be fitted into a tibial canal;
   b. a tibial load bearing component adapted to approximate the size and shape of a tibial plateau;
   c. an tibial intermediate stem extension for operatively connecting the tibial stem to the tibial load bearing component, the extension comprising a central body having a female taper and a male taper, wherein the female taper has a longitudinal axis and the male taper has a longitudinal axis disposed at an angle relative to the longitudinal axis of the female taper;
   d. a femoral stem adapted to be fitted into a femoral canal; and
   e. a femoral load bearing component adapted to approximate the size and shape of condyles of a femur.

22. The knee implant system of claim 21, wherein the male taper of the tibial intermediate stem extension is integrally-formed with the central body of the tibial intermediate stem extension.

23. The knee implant system of claim 21, wherein the longitudinal axis of the male taper is offset parallel a first distance from the longitudinal axis of the female taper at a second distance from a bottom of the female taper.

24. A method of installing a knee implant comprising:
   a. preparing a proximal portion of the tibia and tibial canal of a patient;
   b. preparing a distal portion of the femur and femoral canal of the patient;
   c. performing trial reduction in order to select a tibial implant and a femoral implant for the tibia and femur, respectively;
   d. introducing the tibial implant into the tibial canal, the tibial implant comprising:
      a tibial stem adapted to be fitted into a tibial canal;
      a tibial load bearing component adapted to approximate the size and shape of a tibial plateau; and
      an tibial intermediate stem extension for operatively connecting the tibial stem to the tibial load bearing component, the extension comprising a central body having a female taper and a male taper, wherein the female taper has a longitudinal axis and the male taper has a longitudinal axis disposed at an angle relative to the longitudinal axis of the female taper; and
   e. introducing the femoral implant into the femoral canal, the femoral implant comprising:
      a femoral stem adapted to be fitted into a femoral canal; and
      a femoral load bearing component adapted to approximate the size and shape of condyles of a femur and operatively connect with the femoral stem.

25. The method of claim 24, wherein the male taper of the tibial intermediate stem extension is integrally-formed with the central body of the tibial intermediate stem extension.

* * * * *